US00PP30077P2

(12) United States Plant Patent
Hanes

(10) Patent No.: US PP30,077 P2
(45) Date of Patent: Jan. 8, 2019

(54) ***PELARGONIUM* PLANT NAMED 'PEQZ0031'**

(50) Latin Name: *Pelargonium interspecific*
Varietal Denomination: PEQZ0031

(71) Applicant: SYNGENTA PARTICIPATIONS AG, Basel (CH)

(72) Inventor: Mitchell E. Hanes, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 12 days.

(21) Appl. No.: 15/731,599

(22) Filed: Jul. 6, 2017

(51) Int. Cl.
*A01H 5/02* (2018.01)

(52) U.S. Cl.
USPC ..... Plt./324
CPC ..... *A01H 5/02* (2013.01)

(58) Field of Classification Search
USPC ..... Plt./324
See application file for complete search history.

*Primary Examiner* — Anne Marie Grunberg
(74) *Attorney, Agent, or Firm* — Dale Skalla

(57) ABSTRACT

A new *Pelargonium* plant named 'PEQZ0031' particularly distinguished by deep rose inflorescences held above the medium-green foliage, very heat and drought tolerant with continuous color through the most extreme summer heat, and exceptional edema tolerance on a well-branched plant habit.

1 Drawing Sheet

Latin name of the genus and species of the plant claimed: *Pelargonium interspecific.*

Varietal denomination: 'PEQZ0031'.

BACKGROUND OF THE NEW PLANT

The present invention comprises a new *Pelargonium*, botanically known as *Pelargonium interspecific*, and hereinafter referred to by the variety name 'PEQZ0031'.

'PEQZ0031' is a product of a planned breeding program. The new cultivar 'PEQZ0031' has deep rose inflorescences held above the medium-green foliage, very heat and drought tolerant with continuous color through the most extreme summer heat, and exceptional edema tolerance on a well-branched plant habit.

'PEQZ0031' originates from a hybridization in a controlled breeding program made in September 2011 in a greenhouse in Guatemala. The female parent was an unpatented, proprietary plant of *P. interspecific* parentage, identified as '10998-2' with burgundy flowers and a more open plant habit when compared to 'PEQZ0031'.

The male parent of 'PEQZ0031' was a patented, proprietary plant of *P. interspecific* parentage, identified as Calliope Burgundy '10972-6' also with burgundy flowers and with larger leaves and a larger plant than 'PEQZ0031'. The resultant seed was sown in March 2012.

'PEQZ0031' was selected as one flowering plant within the progeny of the stated cross in July 2012 in a greenhouse in Gilroy, Calif.

The first act of asexual reproduction of 'PEQZ0031' was accomplished when vegetative cuttings were propagated from the initial selection in the June 2012 in a greenhouse in Gilroy, Calif.

BRIEF SUMMARY OF INVENTION

Horticultural examination of plants grown from cuttings of the plant initiated in June 2012 in Gilroy, Calif., and continuing thereafter, has demonstrated that the combination of characteristics as herein disclosed for 'PEQZ0031' are firmly fixed and are retained through successive generations of asexual reproduction.

'PEQZ0031' has not been observed under all possible environmental conditions. The phenotype may vary significantly with variations in environment such as temperature, light intensity, and day length.

A Plant Breeder's Right for this cultivar has not been applied for. 'PEQZ0031' has not been made publicly available prior to the effective filing date of this application, notwithstanding any disclosure that may have been made less than one year prior to the effective filing date of this application by the inventor or another who obtained 'PEQZ0031' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawing shows typical flower and foliage characteristics of 'PEQZ0031' with colors being as true as possible with an illustration of this type.

Figure 1:
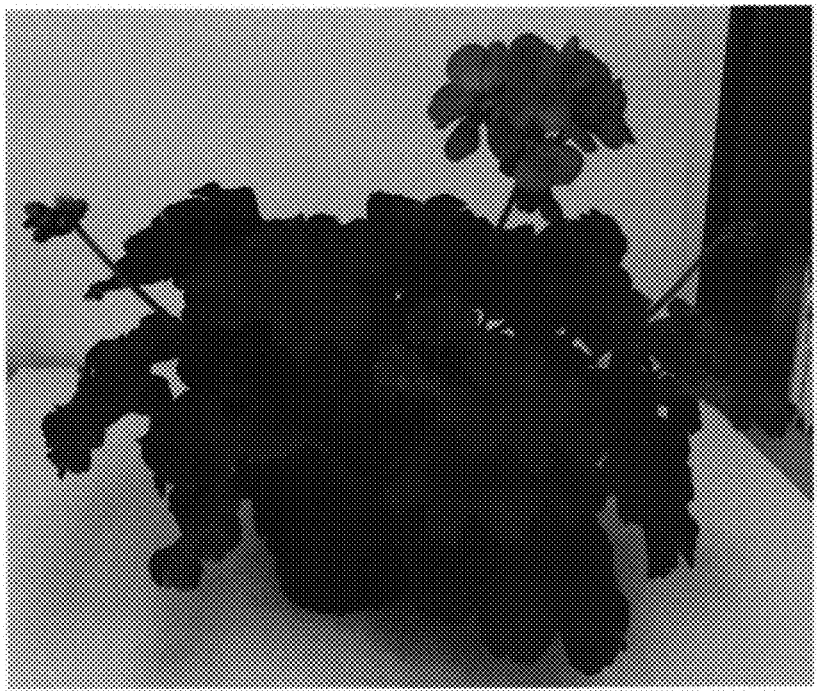
Figure 2:
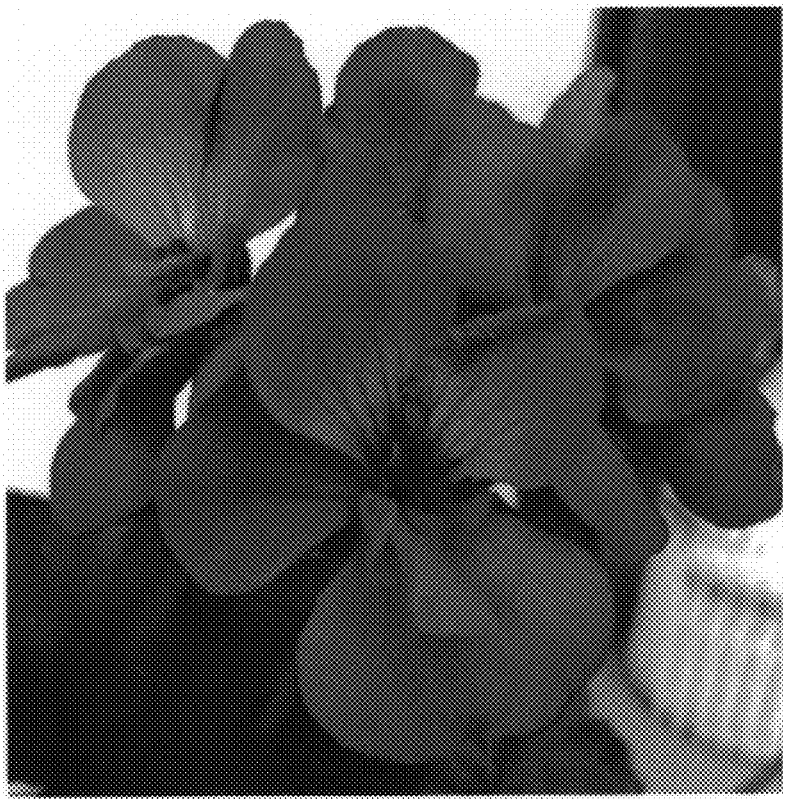

The photographic drawing shows in FIG. 1, 3 flowering plants of the new variety and in FIG. 2, a close-up of an inflorescence.

DETAILED BOTANICAL DESCRIPTION

The plant descriptions and measurements were taken in Gilroy, Calif. in late May 2017 under natural light. These plants were approximately 12 weeks old and were grown in a 4 inch container in a greenhouse trial. The photographs were taken in June 2017.

Color references are made to The Royal Horticultural Society Colour Chart (R.H.S.) 2001.

TABLE 1

DIFFERENCES BETWEEN THE NEW VARIETY 'PEQZ0031' AND A MOST SIMILAR VARIETY

| | 'PEQZ0031' | 'PEQZ0002' (U.S. Plant Pat. No. 23,404) |
|---|---|---|
| Floret size: | smaller | larger |
| Floret petal color: | Deep rose | Lavender rose |
| Umbel diameter size: | Similar | Similar |
| Peduncle length: | Shorter | Longer |
| Flowers: | More | Less |
| Leaves: | Smaller | larger |

Plant:

*Form, growth and habit.*—Upright, outwardly spreading and rounded growth habit, heat and drought tolerant with continuous color through the most extreme summer heat, edema tolerance, well-branched plant habit.

*Plant height.*—13-16 cm.

*Plant height (inflorescence included).*—18-24 cm.

*Plant width.*—38-42 cm.

Roots:

*Number of days to initiate roots.*—15-18 days at about 22 degrees C.

*Number of days to produce a rooted cutting.*—21-23 days at 22 degrees C.

*Type.*—Fine, fibrous, free branching.

*Color.*—RHS N155B but whiter.

Foliage:

*Immature leaf, color upper surface.*—Closest to RHS 144A with a slightly lighter mottling.

*Immature leaf, lower surface.*—Closest to RHS 144A.

*Mature leaf, color upper surface.*—Closest to RHS 137A with slightly lighter mottling.

*Mature leaf, color lower surface.*—Closest to RHS 137C.

*Length.*—8-9.5 cm.

*Width.*—9-10.5 cm.

*Shape.*—Cordate.

*Base shape.*—Cordate.

*Apex shape.*—Acute.

*Margin.*—Slightly dentate.

*Texture upper side.*—Hirsute.

*Texture lower side.*—Hirsute.

*Leaf zonation color.*—None.

*Color of veins, upper surface.*—RHS 137C becoming indistinct.

*Color of veins, lower surface.*—RHS 137C becoming indistinct.

*Pattern of veining.*—Palmate.

*Petiole color.*—RHS 137C.

*Petiole length.*—6-9.0 cm.

*Diameter of petiole.*—0.2 cm.

*Texture.*—Pilose, hirsute, glandular hairs.

Stem:

*Quantity of branches.*—5.

*Color of stem.*—Between RHS 144A and RHS 144B.

*Length of stem.*—10-14.0 cm.

*Diameter.*—0.5-0.7 cm.

*Length of internodes.*—3-4.5 cm.

*Texture.*—Sparsely hirsute, pilose, glandular hairs.

Peduncle:

*Color of peduncle.*—RHS 137D.

*Length of peduncle.*—14-16 cm.

*Peduncle diameter.*—0.3-0.35 cm.

*Texture.*—Hirsute, glandular hairs.

Pedicel:

*Color of pedicel.*—Between RHS 187C.

*Length of pedicel.*—2.4-3.0 cm.

*Diameter of pedicel.*—0.1-15 cm.

*Texture.*—Sparsely pilose, glandular hiars.

Bud (just before opening):

*Color.*—Closest to RHS 74A.

*Length.*—1.5-1.6 cm.

*Width.*—0.8-0.9 cm.

*Shape.*—Elliptical.

Inflorescence:

*Type.*—Umbel; semi-spherical or nearly semi-spherical.

*Lastingness of individual flowers.*—7-9 days at 18° C. temperature.

*Number of inflorescences per plant.*—2, with 2-4 immature umbels in various stages.

*Fragrance.*—None.

*Umbel diameter.*—8-9 cm.

*Umbel depth.*—5-6 cm.

Corolla:

*Form.*—Semi-double.

*Number of petals.*—7-8.

*Diameter of flower.*—About 4.5 cm.

*Depth of flower.*—2-2.5 cm.

*Color upper petals, upper surface.*—Between RHS 74A/B but brighter and more purple; between veins RHS155D from base to mid.

*Color upper petals, lower surface.*—Closest to RHS 74B with RHS 61B veins.

*Length of upper petals.*—3.0 cm.

*Width of upper petals.*—2.0 cm.

*Color lower petals, upper surface.*—Closest to RHS 74A but brighter and more purple.

*Color lower petals, lower surface.*—Closest to RHS 58B.

*Length of lower petals.*—2.7 cm.

*Width of lower petals.*—2.2 cm.

*Petal shape.*—Obovate to spathulate.

*Apex shape.*—Rounded.

*Margin.*—Entire.

*Base.*—Attenuate.

*Petal texture.*—Papillose on both surfaces.

Calyx:

*Number of sepals.*—5.

*Color of sepals.*—RHS 144A with RHS 187D at base diminishing towards tip.

*Length of sepals.*—1.2 cm.

*Width of sepals.*—0.3-0.5 cm.

*Sepal shape.*—Lanceolate to linear.

*Apex shape.*—Acute.

*Margins.*—Mostly fused.

*Texture, upper surface.*—Glabrous.

*Lower surface.*—Glandular hairs, hirsute.

Reproductive organs:

Gynoecium:

*Pistil.*—1.

*Length.*—0.9 cm.

*Style color.*—Closest to RHS 60A.

*Style length.*—0.4 cm.

*Stigma color.*—Closest to RHS 60A.

*Ovary color.*—Between RHS 144A and RHS 144B.

*Ovary length.*—0.5 cm.

*Ovary diameter.*—0.2 cm.

Androecium:

*Number of stamens.*—7.

*Color of filaments.*—RHS 74B with RHS N155C basally.

*Length filaments.*—0.8 cm.

*Anther color.*—Between RHS 25B and RHS 25C with a light mottling of RHS N57B.

*Length of anthers.*—0.2 cm.

*Color of pollen.*—RHS 25B.

*Pollen amount.*—Normal.

*Fertility/seed set.*—Has not been determined to date.

*Disease/pest resistance.*—Has not been determined to date.

What is claimed is:

1. A new and distinct variety of *Pelargonium* plant named 'PEQZ0031' substantially as illustrated and described herein.

* * * * *